United States Patent [19]

Matsushima et al.

[11] Patent Number: 5,463,128

[45] Date of Patent: Oct. 31, 1995

[54] 1,4-BIS(4,4-DIPHENYL-1,3-BUTADIENYL)BENZENE DERIVATIVE AND ELECTROPHOTOGRAPHIC PHOTORECEPTOR USING THE SAME

[75] Inventors: Yoshimasa Matsushima; Toshimitsu Hagiwara, both of Kanagawa, Japan

[73] Assignee: Takasago International Corporation, Tokyo, Japan

[21] Appl. No.: 233,434

[22] Filed: Apr. 28, 1994

[30] Foreign Application Priority Data

Apr. 28, 1993 [JP] Japan .................................. 5-123105

[51] Int. Cl.$^6$ ...................... C07C 211/43; C07C 211/54
[52] U.S. Cl. ............................. 564/452; 430/59; 430/73; 430/74
[58] Field of Search ............................. 564/330; 430/59, 430/73, 74

[56] References Cited

U.S. PATENT DOCUMENTS

| | | | |
|---|---|---|---|
| 4,892,949 | 1/1990 | Sasaki | 564/315 X |
| 4,922,020 | 5/1990 | Gregory et al. | 564/330 |
| 4,971,874 | 11/1990 | Ueda | 430/58 |
| 5,100,985 | 3/1992 | Allen | 526/245 |

FOREIGN PATENT DOCUMENTS 1284858 11/1989 Japan .

OTHER PUBLICATIONS

McDonald et al, Chemical Abstracts, vol. 54 (1960) 24529a.
Suzuki et al, Chemical Abstracts, vol. 113 (1990) 221304.
Mishima et al, Chemical Abstracts, vol. 116 (1992) 140099.
Drefahl, et al., "1.4–Diaryl–butadien und 1.1–Diphenyl–r–aryl–butadiene", Untersuchungen über Stilben, XXXVIII, pp. 1799–1809 (1960).

*Primary Examiner*—Richard L. Raymond
*Attorney, Agent, or Firm*—Sughrue, Mion, Zinn, Macpeak & Seas

[57] ABSTRACT

A 1,4-bis(4,4-diphenyl-1,3-butadienyl)benzene derivative represented by formula (I):

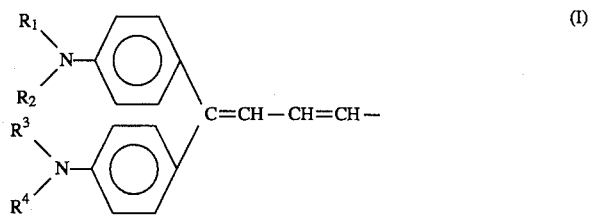

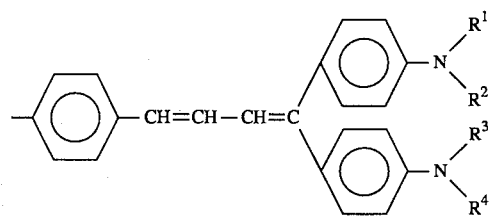

wherein $R^1$, $R^2$, $R^3$, and $R^4$ each independently represents a lower alkyl group which may be substituted, an aralkyl group which may be substituted, or an aryl group which may be substituted, and an electrophotographic photoreceptor using the compound are disclosed. The photoreceptor provides a high carrier drift mobility.

2 Claims, 1 Drawing Sheet

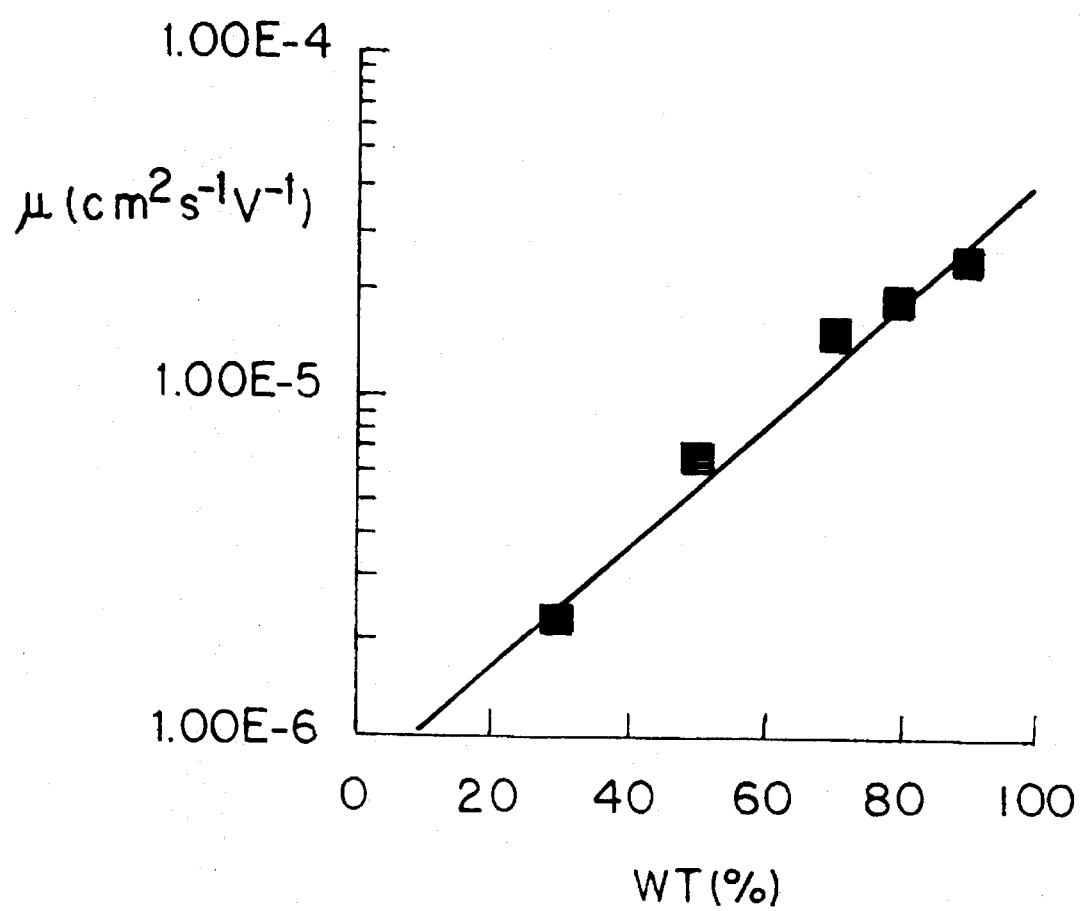
FIGURE

1,4-BIS(4,4-DIPHENYL-1,3-BUTADIENYL)BENZENE DERIVATIVE AND ELECTROPHOTOGRAPHIC PHOTORECEPTOR USING THE SAME

FIELD OF THE INVENTION

The present invention relates to a novel compound, 1,4-bis(4,4-diphenyl-1,3-butadienyl)benzene derivative, a charge transporting material containing the novel compound, and an electrophotographic photoreceptor comprising a charge transporting layer containing the charge transporting material.

BACKGROUND OF THE INVENTION

Recently, as an inorganic photoconductive material, amorphous silicon, amorphous selenium, cadmium sulfide, zinc oxide, etc., are used, but some of these materials are expensive owing to the difficulty of the production thereof and some of them cause a problem from the view point of environmental protection owing to the toxicity of them.

On the other hand, as an organic photoconductive material, in particular, a function separating type light-sensitive material comprising a combination of a charge generating material and a charge transporting material has been positively proposed (e.g., U.S. Pat. No. 3,791,826). In the system, by using a material showing a high carrier generation efficiency as the charge generating material and combining the charge generating material and a material having a high charge transportability as a charge transporting material, there is a possibility of obtaining an electrophotographic photoreceptor having a high sensitivity.

In these materials, the charge transporting material is required to efficiently receive carriers generated in the charge generating material by the irradiation of light under the application of an electric field, quickly transport the carriers in the photoreceptor layer, and quickly erase the surface carrier.

The transferring velocity of a carrier per unit electric field is called carrier drift mobility. A high carrier drift mobility means that the carrier transfers quickly in the charge transporting layer.

The carrier drift mobility is specific to the charge transporting material, and hence in order to attain the high carrier drift mobility, it is necessary to use a material showing a high carrier drift mobility. The carrier drift mobility of conventional materials has not yet reached a sufficient level at present.

On the other hand, since carrier drift mobility depends upon the concentration of the charge transporting material, a method of increasing the concentration of a charge transporting material in a charge transporting layer is employed. The case that the concentration of a charge transporting material becomes the highest is the case that the charge transporting layer is formed by the charge transporting material only and such a charge transporting layer is formed by a vapor deposition method, etc. For example, an organic electroluminescence (EL) device, etc., is prepared by the method as described above [e.g., C. W. Tang and S. A. VanSlyke, *Appl. Phys. Lett.*, 51, 913(1987)].

However, in the case of forming such a charge transporting layer containing a charge transporting material at a high concentration, there are problems of the deposition of crystals and the formation of pin holes, whereby it is difficult to form a uniform layer.

Also, even when the characteristics of both the charge generating material and the charge transporting material are good, it is important that the injection of carriers from the charge generating material into the charge transporting material, that is, the injection of electrostatic charges from the charge generating layer into the charge transporting layer, be carried out with good efficiency. The injection of the carrier depends upon the characteristics of the interface between a charge generating material (or a charge generating layer) and a charge transporting material (or a charge transporting layer) and hence there is not identity between the kinds of the materials being used. As described above, various conditions are required for a charge transporting material.

Hitherto, as a charge transporting material, for example, a distyryl compound represented by the following formula (II) is proposed in JP-A-63-269158 (the term "JP-A" as used herein means an "unexamined published Japanese patent application":

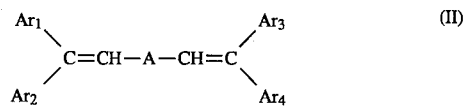

wherein $Ar_1$ to $Ar_4$ each independently represents an alkyl group, an aralkyl group, an aromatic hydrocarbon group which may have a substituent, or an aromatic heterocyclic group which may have a substituent and A represents an alkyl group, an aralkyl group, an aryl group or a heterocyclic group, wherein each group may have a substituent.

Also, JP-A-1-284858 discloses a styryl compound represented by the following formula (III):

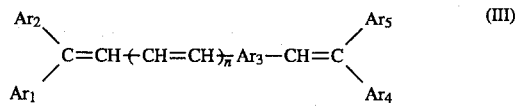

wherein $Ar_1$ represents an alkyl group, an aralkyl group, an aryl group which may have a substituent, or a heterocyclic group which may have a substituent; $Ar_4$ represents a hydrogen atom, an alkyl group, an aralkyl group, or an aryl group which may have a substituent; $Ar_2$ and $Ar_5$ each represents an aryl group which may have a substituent, an aromatic polycyclic group, or a heterocyclic group; $Ar_3$ represents an arylene group which may have a substituent or a divalent heterocyclic group which may have a substituent; n represents 1 or 2; and said $Ar_1$ and $Ar_2$ and said $Ar_4$ and $Ar_5$ may combine with each other to form a ring.

Also, 1,4-bis(4,4-diphenyl-1,3-butadienyl)benzene having a structure near the styryl compound described above is described in *Chem. Ber.*, 93, 1799–1809(1960), but the use of the compound for an electrophotographic photoreceptor is not stated. When the compound is intended for use as an electrophotographic photoreceptor, the solubility of the compound in a binder polymer is poor and hence the compound is hard to utilize.

As other compounds, for example, 1,4-bis[4-(p-dimethylaminophenyl)-1,3-butadienyl]benzene shown by the following formula

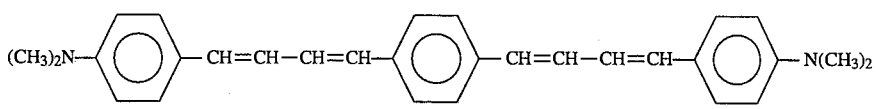

and 1,4-bis[2-(p-dimethylaminophenyl)vinyl]benzene shown by the following formula

are known but the solubility of these compounds in a binder polymer is also poor.

In the case of the conventional compounds as described above, when more than about 2 parts by weight of the compound is added to 1 part by weight of a binder polymer, there are problems that the solubility of the compound in the binder polymer is poor and even when the compound is dissolved in the binder polymer, in the case of forming a film or layer, the compound is crystallized, pin holes are formed, and the film or the layer is whitened or becomes brittle, and hence there is a restriction on the addition amount in the case of using the compound.

Thus, the development of a new material which is stable even when the addition amount is increased and can show a high carrier drift mobility has been desired.

SUMMARY OF THE INVENTION

The object of the present invention is to provide a new material as a charge transporting material, which is stable in the case of forming a film even when the addition amount is increased, can show a high carrier drift mobility, and is excellent in various characteristics in the case of forming an electrophotographic photoreceptor.

As the result of making various investigations on various compounds under the circumstances mentioned above, the inventors have discovered that the object described above can be attained by a 1,4-bis(4,4-diphenyl-1,3-butadienyl-)benzene derivative represented by the following formula (I):

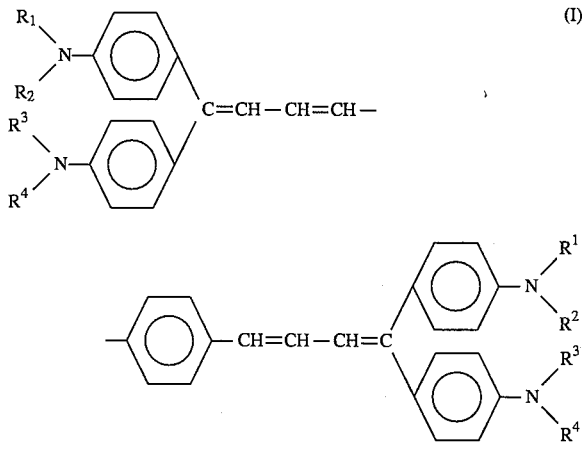

wherein $R^1$, $R^2$, $R^3$, and $R^4$ each independently represents a lower alkyl group which may be substituted, an aralkyl group which may be substituted, or an aryl group which may be substituted, and have succeeded in accomplishing the present invention.

Thus, according to one aspect of the present invention, there is provided the novel 1,4-bis(4,4-diphenyl-1,3-butadienyl)benzene derivative represented by the formula (I) described above.

According to another aspect of the present invention, there is provided a charge transporting material containing the compound shown by the formula (I) described above.

According to still another aspect of the present invention, there is provided an electrophotographic photoreceptor comprising a charge transporting layer containing the charge transporting material.

BRIEF DESCRIPTION OF THE DRAWING

The figure is a graph showing the relation of the concentration of the compound of the present invention in the charge transporting layer and carrier drift mobility.

DETAILED DESCRIPTION OF THE INVENTION

The the present invention is now described in detail.

In the compound of the present invention shown by the formula (I) described above, $R^1$, $R^2$, $R^3$, and $R^4$ each independently represents a lower alkyl group which may be substituted, an aralkyl group which may be substituted, or an aryl group which may be substituted.

As the lower alkyl group, there are alkyl groups having from 1 to 4 carbon atoms such as methyl, ethyl, propyl, iso-propyl, n-butyl, sec-butyl, iso-butyl, tert-butyl, etc.

The lower alkyl group may be substituted with a lower alkoxy group or a halogen atom.

Those substituted lower alkyl groups include methoxymethyl, ethoxymethyl, propoxymethyl, tert-butoxy-methyl, methoxyethyl, methoxypropyl, methoxybutyl, chloromethyl, bromomethyl, chloroethyl, etc.

As the aralkyl group which may be substituted, there is a benzyl group which may be substituted with a lower alkyl group, a lower alkoxy group or a halogen atom.

Those benzyl groups which may be substituted include benzyl, 2-methylbenzyl, 3-methylbenzyl, 4-methylbenzyl, 3-ethylbenzyl, 4-ethylbenzyl, 4-propylbenzyl, 4-tertbutylbenzyl, 2-methoxybenzyl, 3-methoxybenzyl, 4methoxybenzyl, 3-ethoxybenzyl, 4-ethoxybenzyl, 4propoxybenzyl, 4-tert-butoxybenzyl, 2-chlorobenzyl, 3chlorobenzyl, 4-chlorobenzyl, 3-bromobenzyl, 4-bromobenzyl, 2,4-dibromobenzyl, etc.

Also, as the aryl group which may be substituted, there is a phenyl group which may be substituted with a lower alkyl group, a lower alkoxy group or a halogen atom.

Those phenyl groups which may be substituted include phenyl, 2-methylphenyl, 3-methylphenyl, 4-methylphenyl, 2,4-dimethylphenyl, 4-methoxyphenyl, 4-ethoxyphenyl, 4-tertbutoxyphenyl, 4-chlorophenyl, 4-bromophenyl, etc.

The lower alkoxy group described above as a substituent includes methoxy, ethoxy, propoxy, tert-butoxy, etc.

The halogen atom described above as a substituent includes a fluorine atom, chlorine atom, bromine atom, iodine atom, etc.

Furthermore, as specific examples of the preferred compounds of the present invention shown in the formula (I), there are the compounds shown by Table 1 and Table 2 below but the compounds of the formula (I) are not limited to these compounds.

In addition, in the tables, Me shows methyl, Et ethyl, Pr propyl, n-Bu n-butyl, and Ph phenyl.

TABLE 1

| Compound | $R^1$ | $R^2$ | $R^3$ | $R^4$ |
|---|---|---|---|---|
| 1 | Me | Me | Me | Me |
| 2 | Et | Me | Me | Me |
| 3 | Pr | Me | Me | Me |
| 4 | Me | Me | Et | Et |
| 5 | Me | Me | Pr | Pr |
| 6 | Me | Et | Me | Et |
| 7 | Et | Et | Et | Et |
| 8 | Et | Et | Pr | Pr |
| 9 | Et | Et | n-Bu | n-Bu |
| 10 | Pr | Pr | Pr | Pr |
| 11 | Pr | Pr | n-Bu | n-Bu |
| 12 | n-Bu | n-Bu | n-Bu | n-Bu |
| 13 | n-Bu | Pr | n-Bu | Pr |
| 14 | Ph | Ph | Me | Me |
| 15 | Ph | Ph | Et | Et |
| 16 | Ph | Ph | Pr | Pr |
| 17 | Ph | Ph | n-Bu | n-Bu |
| 18 | Ph | Me | Me | Me |
| 19 | Ph | Et | Et | Et |
| 20 | Ph | n-Bu | n-Bu | n-Bu |
| 21 | Ph | Pr | Pr | Pr |
| 22 | Ph | Ph | Ph | Ph |
| 23 | $PhCH_2$ | $PhCH_2$ | Me | Me |
| 24 | $PhCH_2$ | $PhCH_2$ | Et | Et |
| 25 | $PhCH_2$ | $PhCH_2$ | Et | Et |
| 26 | $PhCH_2$ | $PhCH_2$ | n-Bu | n-Bu |
| 27 | $PhCH_2$ | $PhCH_2$ | Ph | Ph |
| 28 | $PhCH_2$ | $PhCH_2$ | $PhCH_2$ | $PhCH_2$ |

TABLE 2

| Compound | $R^1$ | $R^2$ | $R^3$ | $R^4$ |
|---|---|---|---|---|
| 29 | 4-Me-C₆H₄– | 4-Me-C₆H₄– | C₆H₅– | C₆H₅– |
| 30 | 4-Et-C₆H₄– | 4-Et-C₆H₄– | C₆H₅– | C₆H₅– |
| 31 | 2,4-(Me)₂-C₆H₃– | C₆H₅– | 2,4-(Me)₂-C₆H₃– | C₆H₅– |
| 32 | 2-Me-C₆H₄-CH₂– | 2-Me-C₆H₄-CH₂– | Me | Me |
| 33 | 2-Me-C₆H₄-CH₂– | 2-Me-C₆H₄-CH₂– | C₆H₅– | C₆H₅– |
| 34 | 2-Me-C₆H₄-CH₂– | 2-Me-C₆H₄-CH₂– | C₆H₅-CH₂– | C₆H₅-CH₂– |

TABLE 2-continued

| Compound | R¹ | R² | R³ | R⁴ |
|---|---|---|---|---|
| 35 | 3-methylbenzyl | 3-methylbenzyl | Me | Me |
| 36 | 3-methylbenzyl | 3-methylbenzyl | phenyl | phenyl |
| 37 | 3-methylbenzyl | 3-methylbenzyl | benzyl | benzyl |
| 38 | 4-methylbenzyl | 4-methylbenzyl | Me | Me |
| 39 | 4-methylbenzyl | 4-methylbenzyl | phenyl | phenyl |
| 40 | 4-methylbenzyl | 4-methylbenzyl | benzyl | benzyl |

The 1,4-bis(4,4-diphenyl-1,3-butadienyl)benzene derivatives of the present invention shown by the formula (I) described above can be easily synthesized according to, for example, the following reaction formula 1:

Reaction Formula 1:

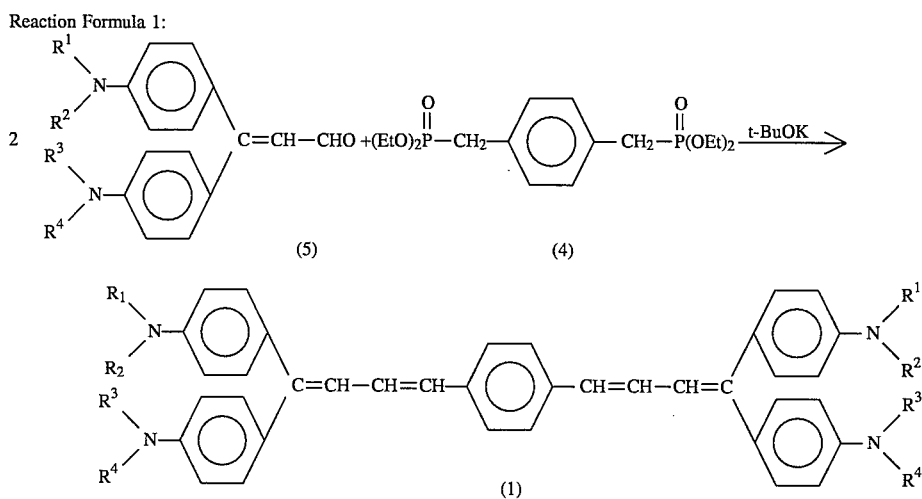

(In the above formulae, R¹, R², R³, R⁴, and Et have the same meaning as described above and t-Bu means tert-butyl.)

That is, the desired compound (1) can be easily produced by reacting p-xylene-α,α'-diylbis(dialkylphosphonate) (4) and 2 mol times of 3,3-diphenylacrolein compound (5) in the presence of a base at a temperature of from about room temperature to 80° C.

As the base being used, there are alcoholates such as sodium methoxide, sodium tert-butoxide, potassium tertbutoxide, etc.

Also, in the above reaction, a solvent is used and as the solvent being used, there are lower alcohols such as methanol, ethanol, etc.; ethers such as 1,2-dimethoxyethane, diethyl ether, tetrahydrofuran, dioxane, etc.; hydrocarbons such as toluene, xylene, etc.; and aprotic polar solvents such as dimethyl sulfoxide (DMSO), N,N-dimethylformamide (DMF), N-methylpyrrolidone, etc.

By using the compound (I) of the present invention for an electrophotographic photoreceptor, a high carrier drift mobility can be obtained.

Practically, in an electrophotographic photoreceptor comprising an electrically conductive support having formed thereon a photosensitive layer including a charge generating layer and a charge transporting layer, the compound (1) of the present invention is used for the charge transporting layer as a charge transporting material.

The charge transporting layer of the present invention can be formed as a molecular thin film of the compound (I) of the present invention by vapor depositing the compound (I) as it is or by coating a solution obtained by dissolving the compound (I) in a proper solvent followed by drying.

Or, in the case of requiring mechanical strength, etc., the charge transporting layer is formed by coating a solution obtained by dissolving the compound (I) of the present invention in a proper solvent together with a binder on an electrically conductive substrate or a charge generating layer formed on the substrate followed by drying.

As the binder being used in such a case, there are, for example, polyacrylate, polyamide, polymethacrylate, a polyvinyl chloride resin, a polyvinyl acetate resin, an epoxy resin, a polyester, polycarbonate, polyurethane, polystyrene, and the copolymers thereof. Also, as polymers other than the insulating polymers as described above, organic photoconductive polymers such as polyvinylcarbazole, polyvinylanthracene, polyvinylene, etc., can be used.

There is no particular restriction on the compounding ratio of the binder and the compound (I) of the present invention and they may be compounded with an optional ratio but it is desirable that the amount of compound (I) of the present invention be as large as possible.

Practically, the compounding amount of the compound (I) of the present invention can be from 10 to 1,000 parts by weight to 100 parts by weight of the binder. That is, in the case of using a conventional charge transporting material, when more than about 2 parts by weight of the charge transporting material is used to 1 part by weight of a binder, there is a problem about the stability of the layer formed but in the case of using the compound (I) of the present invention, even when about 10 parts by weight of the compound (I) of the present invention is added to 1 part by weight of the binder, the layer formed is uniform and stable.

There is no particular restriction about the solvent being used but organic solvents can be used. That is, alcohols such as methanol, ethanol, isopropanol, etc.; ketones such as acetone, methyl ethyl ketone, cyclohexanone, etc.; amides such as N,N-dimethylformamide, N,N-dimethylacetamide, etc.; sulfoxides such as dimethylsulfoxide, etc.; ethers such as tetrahydrofuran, dioxane, ethylene glycol dimethyl ether, etc.; esters such as ethyl acetate, methyl acetate, etc.; aliphatic halogenated hydrocarbons such as methylene chloride, chloroform, 1,2-dichloroethane, dichloroethylene, carbon tetrachloride, trichloroethylene, etc.; and aromatic compounds such as benzene, toluene, xylene, chlorobenzene, dichlorobenzene, etc., can be used.

As the electrically-conductive substrate being used for the electrophotographic photoreceptor of the present invention, a sheet-form or drum-form foil or plate of a metal such as copper, aluminum, silver, iron, zinc, nickel, etc., or an alloy thereof is used. Also, a plastic film or cylinder vacuum evaporated or electrolytically plated with the foregoing metal or a substrate such as a paper or a plastic film having formed thereon a layer of an electrically conductive compound such as an electrically conductive polymer, indium oxide, tin oxide, etc., by coating or by a vapor-deposition is used as the electrically conductive substrate.

Coating for preparing the electrically conductive substrate described above can be carried out using a dip coating method, a spray coating method, a spinner coating method, a wire bar coating method, a blade coating method, a roller coating method, a curtain coating method, etc.

Drying of the coated layer is preferably carried out by a method of drying by heating after drying at room temperature. Drying by heating is preferably carried out in the range of a temperature of from 30° C. to 200° C. for from 5 minutes to 2 hours under a windless state or under air blowing.

Furthermore, if necessary, the charge transporting layer of the present invention may contain various additives. For example, plasticizers such as biphenyl, m-terphenyl, dibutyl phthalate, etc.; surface lubricants such as silicone oils, graft type silicone polymers, various fluorocarbons, etc.; electric potential stabilizers such as dicyanovinyl compounds, carbazole derivatives, etc.; monophenol series antioxidants such as 2-tert-butyl-4-methoxyphenol, etc.; bisphenol series antioxidants; amine series antioxidants such as 1,4-diazabicyclo[2.2.2]octane; and salicylic acid series antioxidants can be added.

Also, if necessary, another charge transporting material can be added to the charge transporting layer in the present invention.

The thickness of the charge transporting layer formed is from 2 to 40 μm, and preferably from 5 to 30 μm.

By electrically connecting the charge transporting layer obtained to a charge generating layer, the charge transporting layer can have the function of receiving the carriers injected from the charge generating layer in the existence of an electric field and transporting the carriers to the surface of the photosensitive layer.

In this case, the charge transporting layer may be laminated on the charge generating layer or under the charge generating layer but it is preferred that the charge transporting layer is laminated on the charge generating layer.

In the photosensitive layer in the present invention, if necessary, a protective layer may be formed on the layer thus formed.

As the charge generating layer, a vapor-deposited layer or a coated layer formed by using an inorganic charge generating material such as selenium, selenium-tellurium, amorphous silicon, etc., or organic charge generating materials such as cationic dyes (e.g., pyrylium salt series dyes, thiapyrylium salt series dyes, azulenium salt series dyes, thiacyanine series dyes, and quinocyanine series dyes), squarylium salt series pigments, phthalocyanine series pigments, anthanthrone series pigments, polycyclic quinone pigments (e.g., dibenzpyrene quinone series pigments and pyranthrone series pigments), indigo series pigments, quinacridone series pigments, azo pigments, pyrrolopyrrole series pigments, etc., can be used. In addition to these materials described above, any materials which absorb light and generate carriers at a high efficiency .can be used.

In the manner as described above, the electrophotographic photoreceptor containing the 1,4-bis(4,4-diphenyl-1,3-butadienyl)benzene derivative shown by the formula (I), i.e., the compound (I) of the present invention in the charge transporting layer, can be obtained.

The 1,4-bis(4,4-diphenyl-1,3-butadienyl)benzene derivative, i.e., the compound (I) of the present invention, can be widely used not only for the electrophotographic photoreceptor but also as charge transporting materials such as an organic electroluminescence (EL) material, etc.

The following examples are intended to illustrate the present invention more in detail but not to limit it in any way.

In addition, the measurement of the $^1$H-NMR spectra in the examples was carried out by the apparatus Type AM-400 (trade name, manufactured by Bruker, Inc.) (400 MHz, solvent: CDCl$_3$, internal standard substance: tetramethylsilane).

The measurement of SIMS (secondary ion mass spectrometer) spectra was carried out using a Hitachi M80B Double-Focusing Mass Spectrometer (trade name, made by Hitachi, Ltd.), using Xe$^+$ as the primary ion, and using m-nitrobenzyl alcohol as the matrix.

EXAMPLE 1

Synthesis of 1,4-bis(4-p-diethylaminophenyl-4-p-dimethylaminophenyl-1,3-butadienyl)benzene (Illustrative Compound 4)

In 100 ml of DMF were dissolved 2.16 g of 3-p-diethylaminophenyl- 3-p-dimethylaminophenylacrolein and 1.4 g of p-xylene-α,α'-diylbis(diethyl phosphonate), and then 0.83 g of potassium tert-butoxide was added to the solution at room temperature. Thereafter, the reaction was carried out for 4 hours at room temperature with stirring and the reaction mixture was poured into 100 ml of ice-water with stirring. Precipitates thus deposited were collected by filtration, dissolved in benzene, and separated and purified by silica gel column chromatography (eluent: benzene). After distilling off benzene from the effluent, the residue was recrystallized from ethyl acetate to provide 1.42 g (yield 59.0%) of red crystals having a melting point of from 198.0° C. to 200.0° C.

$^1$H-NMR Spectra (δ, ppm): 1.18(t, J=7Hz, 6H), 1.22(t, J=7Hz, 6H), 2.98(s, 6H), 3.02(s, 6H), 3.32 to 3.43(m, 8H), 6.58 to 6.88(m, 15H), 6.93 to 7.28(m, 11H).

SIMS: 715(M+H)$^{+1}$

EXAMPLE 2

Synthesis of 1,4-bis[4,4-bis(p-diethylaminophenyl)-1,3-butadienyl]benzene (Illustrative Compound 7)

In 100 ml of DMF were dissolved 2.5 g of 3,3-bis(p-diethylaminophenyl)acrolein and 1.5 g of p-xylene-α,α'-diylbis(diethyl phosphonate), and then 0.9 g of potassium tert-butoxide was added to the solution at room temperature. Thereafter, the reaction was carried out for 4 hours at room temperature with stirring and the reaction mixture was poured into 100 ml of ice-water with stirring. Then, precipitates thus deposited were collected by filtration, dissolved in benzene, and separated and purified by silica gel column chromatography (eluent: benzene). After distilling off benzene from the effluent, the residue was recrystallized from ethyl acetate to provide 1.74 g (yield 63.0%) of red crystals having a melting point of 201.5° C. to 204.5° C.

$^1$H-NMR Spectra (δ, ppm): 1.17(t, J=7Hz, 12H), 1.22(t, J=7Hz, 12H), 3.40(m, J=7Hz, 16H), 6.55 to 6.69(m, 11H), 6.98 to 7.35(m, 15H).

SIMS: 771(M+H)$^{+1}$

EXAMPLE 3

Synthesis of 1,4-bis[4,4-bis(p-dibutylaminophenyl)-1,3-butadienyl]benzene (Illustrative Compound 12)

In 100 ml of DMF were dissolved 2.21 g of 3,3-bis(p-dibutylaminophenyl)acrolein and 1.0 g of p-xylene-α,α'-diylbis(diethyl phosphonate), and then 0.59 g of potassium tert-butoxide was added to the solution at room temperature. Thereafter, the reaction was carried out for 4 hours at room temperature with stirring and the reaction mixture was poured into 100 ml of ice-water. Then, precipitates thus deposited were collected by filtration, dissolved in benzene, and separated and purified by silica gel column chromatography (eluent: benzene). After distilling off benzene from the effluent, the residue was recrystallized from ethyl acetate to provide 1.42 g (yield 58.8%) of red crystals having a melting point of from 107.0° C. to 111.5° C.

$^1$H-NMR Spectra (δ, ppm): 0.99(m, J=7Hz, 24H), 1.38(m, 16H), 1.60(m, 16H), 3.30(m, 16H), 6.52 to 6.68(m, 15H), 7.28 to 7.72 (m, 11H).

SIMS: 995(M+H)$^{+1}$

EXAMPLE 4

Synthesis of 1,4-bis(4-p-dibenzylaminophenyl-4-p-diethylaminophenyl-1,3-butadienyl)benzene (Illustrative Compound 25)

In 100 ml of DMF were dissolved 2.26 g of 3-p-dibenzylaminophenyl- 3-p-diethylaminophenylacrolein and 1.0 g of p-xylene-α,α'-diylbis(diethyl phosphonate), and 0.74 g of potassium tert-butoxide was added to the solution at room temperature. Thereafter, the reaction was carried out for 4 hours at room temperature with stirring and the reaction mixture was poured into 100 ml of ice-water. Then, precipitates thus deposited were collected by filtration, dissolved in benzene, and separated and purified by silica gel column chromatography (eluent: benzene). After distilling off benzene from the effluent, the residue was recrystallized from ethyl acetate to provide 1.5 g (yield 62.0%) of red crystals having a melting point of from 206.0° C. to 208.0° C.

$^1$H-NMR Spectra (δ, ppm): 1.13 to 1.22(m, 12H), 3.38(m, 8H), 4.67(m, 8H), 6.50 to 6.80(m, 12H), 6.91 to 7.38(m, 24H).

SIMS: 1019(M+H)$^{+1}$

EXAMPLE 5

Synthesis of 1,4-bis[4,4-bis(p-benzylaminophenyl)-1,3-butadienyl]benzene (Illustrative Compound 28):

By following the same procedure as Example 1 except that 3,3-bis(p-dibenzylaminophenyl)acrolein was used in place of 3-p-diethylaminophenyl-3-p-dimethylaminophenyl acrolein of the starting material, 1,4-bis[4,4-bis(p-benzylaminophenyl)- 1,3-butadienyl]benzene having a melting point of from 118° C. to 122° C. was obtained.

$^1$H-NMR Spectra (δ, ppm): 4.77(d, J=9.0Hz, 16H), 6.52 to 7.33(66H).

SIMS: 1259(M+H)$^{+1}$

EXAMPLE 6

Synthesis of 1,4-bis[4-p-(ethylphenylamino)phenyl-4-p-diethylaminophenyl-1,3-butadienyl]benzene (Illustrative Compound 19)

By following the same procedure as Example 1 except that 3-p-(ethylphenylamino)phenyl-3-p-diethylaminophenylacrolein was used in place of 3-p-diethylaminophenyl-3-p-dimethylaminophenylacrolein of the starting material, 1,4-bis[4-p-(ethylphenylamino)phenyl-4-p-diethylaminophenyl-1,3-butadienyl]benzene having a melting point of from 104° C. to 108° C. was obtained.

$^1$H-NMR Spectra (δ, ppm): 1.12 to 1.33(m, 18H), 3.39(m, 8H), 3.82(m, 4H), 6.57 to 7.38 (m, 36H).

SIMS: 867(M+H)$^{+1}$

APPLICATION EXAMPLES 1 TO 4

A mixture of 1 part by weight of r type metal-free phthalocyanine and 1 part by weight of a butyral resin (Polyvinylbutyral BM-1, trade name, made by Sekisui Chemical Co., Ltd.) was kneaded using 30 parts by weight of tetrahydrofuran as a solvent in a ball mill for 5 hours. The pigment dispersion thus obtained was coated on a polyethylene terephthalate (PET) film having vapor-deposited thereon aluminum and dried for 2 hours at 100° C. to form a charge generating layer.

Apart from this, 1 part by weight of each of the Compounds 4, 7, 12, and 25 obtained in Examples 1 to 4 and 1 part by weight of a polycarbonate resin (Polycarbonate Z, trade name, made by Mitsubishi Gas Chemical Company, Inc.) were mixed and dissolved in 8 parts by weight of dichloroethane. Each of the solutions thus obtained was coated on the charge generating layer by a doctor blade and dried for 3 hours at 80° C. to form each charge transporting layer.

The electrophotographic characteristics of each of the electrophotographic photoreceptors thus obtained were measured by a static process using an electropaper analyzer, Type SP-428 (trade name, manufactured by Kawaguchi Denki Seisakusho K.K.).

That is, each photoreceptor was electrostatically charged by corona discharge at −6 kV for 5 seconds and the surface potential $V_0$ (unit: −volt) was measured. Then, after placing the photoreceptor in the dark for 5 seconds, the photoreceptor was irradiated by light of 5 lux emitted from a tungsten lamp, and the light-exposure amount necessary for decaying the surface potential to a half, that is, a half decay light-exposure $E_{1/2}$ (lux-second) and the surface residual potential $V_{R10}$ (−volt) after irradiating the photoreceptor for 10 seconds by light of 5 lux in the illuminance were measured. The results are shown in Table 3 below.

APPLICATION EXAMPLES 5 TO 7

After mixing and dissolving 1 part by weight of each of the Compounds 4, 7, and 12 obtained in Examples 1 to 3 and 1 part by weight of a polycarbonate resin in 8 parts by weight of dichloroethane terephthalate, each solution thus obtained was coated on a polyethylene (PET) film having vapor-deposited thereon aluminum by a doctor blade and dried for 3 hours at 80° C. to form a charge transporting layer.

Furthermore, a translucent metal (Au) electrode was vapor-deposited on the charge transporting layer and the carrier drift mobility was measured.

The measurement of the carrier drift mobility was carried by a time-of-flight technique [S. Tanaka, Y. Yamaguchi, and M. Yokoyama, *Denshishashin (Electrophotography)*, 29,366(1990)] using a nitrogen gas laser having a pulse half value width of 0.9 nsec and a wavelength of 337 nm as the light source.

The results obtained are shown in Table 4 below.

APPLICATION EXAMPLE 8

Compound 7 obtained in Example 2 was added to a polycarbonate resin as a binder in a weight ratio of 30%, 50%, 70%, 80%, or 90% to the polycarbonate resin and was mixed therewith and dissolved therein with dichloroethane of 4 times the amount of the solid components. In these cases, the compound was uniformly dissolved and the solubility of the charge transporting material was high.

Each solution was coated on a polyethylene terephthalate (PET) film having vapor-deposited aluminum by the same manner as in Application Examples 1 to 4 and dried for 3 hours at 80° C. to form each charge transporting layer. When the charge transporting layer containing the charge transporting material at a high concentration as described above, the uniform layer having neither deposition of crystals nor the formation of pin holes could be formed.

Then, a translucent metal (Au) electrode was vapor-deposited on each charge transporting layer and the carrier drift mobility was measured. The results showed that in these characteristics, the excellent characteristics were obtained in each case as compared to the case of using conventional charge transporting materials.

The results are shown in Table 5 and Figure.

COMPARATIVE EXAMPLE 1

Synthesis of 1,4-bis(4,4-diphenyl-1,3butadienyl)benzene (Comparative Compound 41) and the application example thereof In 100 ml of DMF were dissolved 5.53 g of 3,3-diphenylacrolein and 5.0 g of p-xylene-α,α'-diylbis(diethyl phosphonate), and 3.87 g of potassium tert-butoxide was added to the solution at room temperature. Thereafter, the reaction was carried out for 4 hours at room temperature with stirring and the reaction mixture was poured into 100 ml of ice-water with stirring. Then, precipitates thus deposited were collected by filtration, dissolved in benzene, and separated and purified by silica gel column chromatography (eluent: benzene). After distilling off benzene from the effluent, the residue was recrystallized from ethyl acetate to provide 1.00 g (yield 15.6%) of yellow crystals having a melting point of from 237.0° C. to 249.5° C.

$^1$H-NMR Spectra (δ, ppm): 6.51 to 6.80 (m, 12H), 7.00 to 7.35(m, 28H).

An electrophotographic photoreceptor was prepared by the same manner as Application Examples 1 to 4 except that the Comparative Compound 41 thus obtained was used as the charge transporting material and the various characteristics of the electrophotographic photoreceptor were measured by the same manners as described above.

The results obtained are shown in Table 3 below.

TABLE 3

| Application Example | Illustrative Compound | $V_0$ (—V) | $V_{R10}$ (—V) | $E_{1/2}$ (lux · s) |
|---|---|---|---|---|
| 1 | 4 | 746 | 0 | 0.7 |
| 2 | 7 | 526 | 0 | 0.8 |
| 3 | 12 | 1046 | 0 | 1.1 |
| 4 | 25 | 638 | 0 | 0.6 |
| Comparative Ex. 1 | Comparative Compound 41 | 1200 | 260 | 3.8 |

From the results shown in Table 3 above, it can be seen that in Application Examples 1 to 4 using the compounds of the present invention, the surface residual potential $V_{R10}$ after irradiating light for 10 seconds is 0 volt in all the cases, while in the case of using Comparative Compound 41, $V_{R10}$ is 260 volts, and also the compounds of the present invention are very excellent in the charge transportability.

Also, in Application Examples 1 to 4, the half decay light-exposure $E_{1/2}$ are from 0.6 to 1.1 (lux·second), while in the case of using Comparative Compound 41, $E_{1/2}$ is 3.8 (lux·second), which is several times that of the above cases and hence the compounds of the present invention are excellent in the charge transporting ability.

COMPARATIVE EXAMPLE 2

By following the same procedures in Application Examples 5 to 7 except that Comparative Compound 41 obtained in Comparative Example 1 was used as the charge transporting material, a film was prepared but a film having a good quality was not obtained owing to the occurrences of crystallization and whitening, and also the carrier drift mobility could not be measured.

TABLE 4

| Application Example | Illustrative Compound | Carrier Drift Mobil ($10^{-6}$cm$^2$ · V$^{-1}$ · s$^{-1}$) |
|---|---|---|
| 5 | 4 | 3.07 |
| 6 | 7 | 11.2 |
| 7 | 12 | 6.27 |
| Comparative Ex. 2 | Comparative Compound 41 | unmeasurable |

TABLE 5

(Mobility Change to Concentration of Illustrative Compound 7)

| wt (%) | $\mu$ ($10^{-6}$cm$^2$ · s$^{-1}$ · V$^{-1}$) |
|---|---|
| 30 | 2.16 |
| 50 | 6.37 |
| 70 | 14.5 |
| 80 | 18.1 |
| 90 | 24.8 |

As described above, the 1,4-bis(4,4-diphenyl-1,3butadienyl)benzene derivative (I) of the present invention has a good solubility and when a film or layer containing the compound at a high concentration is formed by increasing the addition amount of the compound, a uniform and stabilized film or layer can be formed. Thus, when an electrophotographic photoreceptor is prepared using the compound of the present invention for the charge transporting layer, the charge transporting layer can show a high carrier drift mobility and the electrophotographic photoreceptor has good characteristics of a high sensitivity and giving no residual potential. Thus, the compound (I) of the present invention is an industrially excellent compound.

While the invention has been described in detail and with reference to specific embodiments thereof, it will be apparent to one skilled in the art that various changes and modifications can be made therein without departing from the spirit and scope thereof.

What is claimed is:

1. A 1,4-bis(4,4-diphenyl-1,3-butadienyl)benzene derivative represented by formula (I):

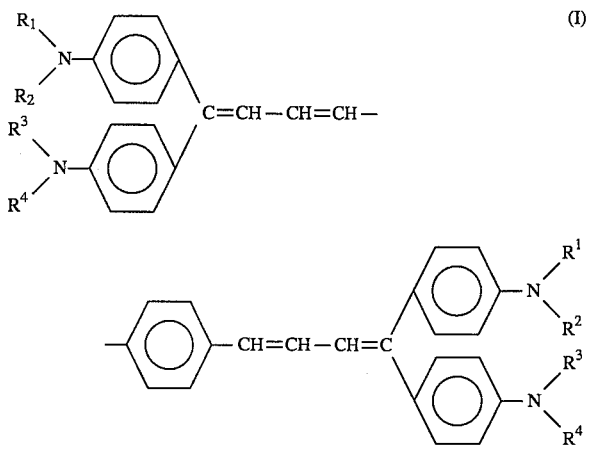

wherein $R^1$, $R^2$, $R^3$, and $R^4$ each independently represents a lower alkyl group which may be substituted with a lower alkoxy group or a halogen atom, an aralkyl group which may be substituted with a lower alkyl group, a lower alkoxy group or a halogen atom, or an aryl group which may be substituted with a lower alkyl group, a lower alkoxy group or a halogen atom.

2. A charge transporting material comprising a 1,4-bis (4,4-diphenyl-1,3-butadienyl) benzene derivative represented by formula (I):

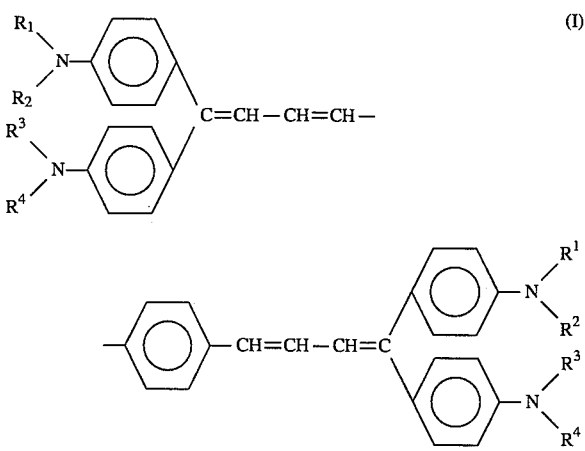

wherein $R^1$, $R^2$, $R^3$, and $R^4$ each independently represents a lower alkyl group which may be substituted with a lower alkoxy group or a halogen atom, an aralkyl group which may be substituted with a lower alkyl group, a lower alkoxy group or a halogen atom, or an aryl group which may be substituted with a lower alkyl group, a lower alkoxy group or a halogen atom.

* * * * *